US008629153B2

(12) United States Patent
Jung

(10) Patent No.: US 8,629,153 B2
(45) Date of Patent: Jan. 14, 2014

(54) USE OF QUINAZOLINE DERIVATIVES FOR THE TREATMENT OF VIRAL DISEASES

(75) Inventor: Birgit Jung, Laupheim (DE)

(73) Assignee: Boehringer Ingelheim International GmbH, Ingelheim am Rhein ( * ) Notice: Subject to any disclaimer, the term of this patent is extended or adjusted under 35 U.S.C. 154(b) by 251 days.

(21) Appl. No.: 13/061,753

(22) PCT Filed: Aug. 13, 2009

(86) PCT No.: PCT/EP2009/060504
§ 371 (c)(1),
(2), (4) Date: May 4, 2011

(87) PCT Pub. No.: WO2010/026029
PCT Pub. Date: Mar. 11, 2010

(65) Prior Publication Data
US 2011/0281860 A1 Nov. 17, 2011

Related U.S. Application Data
(60) Provisional application No. 61/094,106, filed on Sep. 4, 2008.

(30) Foreign Application Priority Data
Sep. 3, 2008 (EP) .................................. 08163578

(51) Int. Cl.
*A61K 31/517* (2006.01)
(52) U.S. Cl.
USPC ...................................................... 514/266.1
(58) Field of Classification Search
USPC ...................................................... 514/266.1
See application file for complete search history.

(56) References Cited

U.S. PATENT DOCUMENTS

| | | |
|---|---|---|
| 6,656,946 B2 | 12/2003 | Himmelsbach et al. |
| 6,924,285 B2 | 8/2005 | Himmelsbach et al. |
| 7,119,084 B2 | 10/2006 | Himmelsbach et al. |
| 7,910,731 B2 | 3/2011 | Himmelsbach et al. |
| 2002/0082271 A1 | 6/2002 | Himmelsbach et al. |
| 2002/0177601 A1 | 11/2002 | Himmelsbach et al. |
| 2004/0048880 A1 | 3/2004 | Himmelsbach et al. |
| 2005/0182043 A1 | 8/2005 | Himmelsbach et al. |
| 2006/0035893 A1 | 2/2006 | Jung et al. |
| 2006/0063752 A1 | 3/2006 | Himmelsbach et al. |
| 2006/0178364 A1 | 8/2006 | Jung et al. |
| 2006/0270672 A1 | 11/2006 | Himmelsbach et al. |
| 2007/0135463 A1 | 6/2007 | Himmelsbach et al. |
| 2009/0017036 A1 | 1/2009 | Jung et al. |
| 2009/0036676 A1 | 2/2009 | Himmelsbach et al. |
| 2009/0203683 A1 | 8/2009 | Himmelsbach et al. |
| 2010/0022505 A1 | 1/2010 | Himmelsbach et al. |
| 2010/0099651 A1 | 4/2010 | Jung et al. |
| 2011/0046148 A1 | 2/2011 | Himmelsbach et al. |

FOREIGN PATENT DOCUMENTS

| | | |
|---|---|---|
| CA | 2575541 A1 | 2/2006 |
| CA | 2601740 A1 | 8/2006 |
| CA | 2631813 A1 | 6/2007 |
| CA | 2667543 A1 | 5/2008 |
| CA | 2711582 A1 | 8/2009 |
| WO | 2005048928 A2 | 6/2005 |
| WO | 2006015775 A2 | 2/2006 |
| WO | 2006082129 A1 | 8/2006 |
| WO | 2006083458 A2 | 8/2006 |
| WO | 2006090163 A1 | 8/2006 |
| WO | 2007068552 A1 | 6/2007 |
| WO | 2008049842 A2 | 5/2008 |
| WO | 2009098061 A1 | 8/2009 |

OTHER PUBLICATIONS

International Search Report for PCT/EP2009/060504 mailed Sep. 29, 2009.
Liu, Kenneth, et al; Epidermal Growth Factor Receptor Signaling to ERK1/2 and STATs Control the Intensity of the Epithelial Inflammatory Responses to Rhinovirus Infection; The Journal of Biological Chemistry (2008) vol. 283, No. 15 pp. 9977-9985.
Monick, Martha, M., et al; Activation of the Epidermal Growth Factor Receptor by Respiratory Syncytial Virus Results in Increased Inflammation and Delayed Apoptosis; The Journal of Biological Chemistry (2005) vol. 280, No. 3 pp. 2147-2158.
Sieczkarski, Sara, B., et al; Role of Protein Kinase C Beta II in Influenza Virus entry Via Late Endosomes: Journal of Virology (2003) vol. 77, No. 1 pp. 460-469.
Song, Jeong Sup, et al; Mucin Secretion in the Rat Tracheal Epithelial Cells by Epidermal Growth Factor and Pseudomonas Aeruginosa Extracts; The Korean Journal of Internal Medicine (2001) vol. 16, No. 3 pp. 167-172.
Wang, Xin, et al; Epidermal Growth Factor Receptor Is a Cellular Receptor for Human Cytomegalovirus; Nature (2003) vol. 424 pp. 456-461.
Yang, Hailin, et al; Antiviral Chemotherapy Facilities Control of Poxvirus Infections Through Inhibition of Cellular Signal Transduction; The Journal of Clinical Investigation (2005) vol. 115, No. 2 pp. 379-387.

*Primary Examiner* — Shengjun Wang
(74) *Attorney, Agent, or Firm* — Michael P. Morris; Edward S. Lazer

(57) ABSTRACT

The present invention relates to the use of quinazoline derivatives, which show EGFR inhibitory activity, for the prevention and/or treatment of virus-induced diseases, preferably virus induced respiratory diseases and exacerbation in chronic airway diseases such as COPD or asthma.

6 Claims, No Drawings

USE OF QUINAZOLINE DERIVATIVES FOR THE TREATMENT OF VIRAL DISEASES

FIELD OF THE INVENTION

The present invention relates to the use of quinazoline derivatives, which show EGFR inhibitory activity, for the prevention and treatment of virus-induced diseases, preferably virus induced respiratory diseases and exacerbations in chronic airway diseases such as COPD or asthma.

BACKGROUND OF THE INVENTION

Chronic airway diseases such as chronic bronchitis including COPD and asthma are characterized by inflammation and increased mucus production. Inflammation and excess mucus production are believed to drive the accelerated decline of lung function in chronic airway diseases.

The increased mucus production is attributed to the remodelling of the airway epithelium in which ciliated cells have been replaced by mucus producing goblet cells. The rarification of ciliated cells impairs the mucociliary clearance. Together with the increased mucus production this leads to mucus plugging of the small airways. An important function of mucociliary clearance is to cleanse the airways from inhaled particulates including viruses which have been trapped in the mucus layer and are then removed from the airways together with the mucus through a coordinated movement of the cilia. In airway diseases such as COPD and asthma, the viruses entrapped in mucus and stuck to the airway epithelium encounter good conditions for infection. Viral infections of the lungs in patients with chronic airway diseases result in an exacerbation of the underlying disease, characterized by an aggravation of the symptoms such as excess mucus production, inflammation and airflow limitation. Patients with exacerbations often need to be hospitalized because they suffer from a dramatic reduction of lung function. Further, in the long term, exacerbations lead to a more rapid and more progressive decline of lung functions compared to patients who do not suffer from exacerbations. The major cause of exacerbations are viral infections of the airways and/or lungs.

It has been demonstrated that inhibition of the epidermal growth factor signalling prevents the excess mucus production and increase in goblet cells. Recently it was shown that EGFR inhibitors can also prevent and/or treat viral infections (WO 2005/048928; Liu Kenneth; Gualano Rosa C; Hibbs Margaret L; Anderson Gary P; Bozinovski Steven Epidermal growth factor receptor signaling to Erk1/2 and STATs control the intensity of the epithelial inflammatory responses to rhinovirus infection. The Journal of Biological Chemistry (2008), 283(15), 9977-85; Monick M M. Cameron K. Staber J. Powers L S. Yarovinsky T O. Koland J G. Hunninghake G W. Activation of the epidermal growth factor receptor by respiratory syncytial virus results in increased inflammation and delayed apoptosis. Journal of Biological Chemistry. 280 (3):2147-58, 2005).

The present invention relates to the prevention and/or treatment of viral infections and exacerbation in chronic airway diseases such as COPD and asthma. Viral infections can be prevented or treated by EGFR inhibitors either by preventing entry of the virus, by inhibition of virus replication and/or by inhibition of symptoms caused by viral infection. Inhibition of virus entry into the cells and/or replication of the virus will reduce the viral load and reduce the severity and duration of an exacerbation. The inhibition of symptoms caused by viral infection comprises inhibition/reduction of influx of inflammatory cells such as macrophages, neutrophils and lymphocytes, the inhibition of the upregulation of the EGF receptor and EGFR ligand, mucus production and inhibition/alleviation of the severity and duration of exacerbations.

It is the object of the present invention to provide an antiviral agent, i.e. an agent for treating and/or preventing viral infections or for treating and/or preventing exacerbation in chronic airway diseases such as COPD and asthma.

DESCRIPTION OF THE INVENTION

Surprisingly it has been found, that the EGFR inhibitors of the present invention that had been optimized for inhibition of mucus production and increase of mucus producing goblet cells also demonstrate very potent anti-viral effects.

Accordingly the invention provides the use of an EGFR inhibitor of general formula (I)

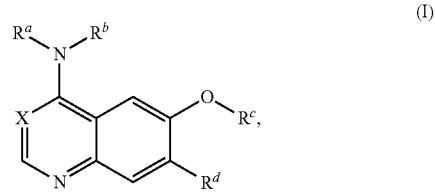

wherein
$R^a$ denotes a hydrogen atom or a $C_{1-4}$-alkyl group,
$R^b$ denotes a phenyl or 1-phenylethyl group, wherein the phenyl nucleus is substituted in each case by the groups $R^1$ to $R^3$, while
  $R^1$ and $R^2$, which may be identical or different, in each case denote a hydrogen, fluorine, chlorine, bromine or iodine atom,
  a $C_{1-4}$-alkyl, hydroxy, $C_{1-4}$-alkoxy, $C_{2-3}$-alkenyl or $C_{2-3}$-alkynyl group,
  an aryl, aryloxy, arylmethyl or arylmethoxy group,
  a heteroaryl, heteroaryloxy, heteroarylmethyl or heteroarylmethoxy group,
  a methyl or methoxy group substituted by 1 to 3 fluorine atoms or
  a cyano, nitro or amino group, and
  $R^3$ denotes a hydrogen, fluorine, chlorine or bromine atom or
  a methyl or trifluoromethyl group,
$R^c$ denotes a cyclobutyl, cyclopentyl or cyclohexyl group which is substituted in each case by a group $R^4$—N—$R^5$, while
  $R^4$ denotes a hydrogen atom or a $C_{1-3}$-alkyl group and
  $R^5$ denotes a hydrogen atom or a $C_{1-3}$-alkyl group,
  an aminocarbonyl-$C_{1-3}$-alkyl, $C_{1-3}$-alkylaminocarbonyl-$C_{1-3}$-alkyl, di-($C_{1-3}$-alkyl)aminocarbonyl-$C_{1-3}$-alkyl, pyrrolidin-1-ylcarbonyl-$C_{1-3}$-alkyl, piperidin-1-ylcarbonyl-$C_{1-3}$-alkyl, homopiperidin-1-ylcarbonyl-$C_{1-3}$-alkyl, morpholin-4-ylcarbonyl-$C_{1-3}$-alkyl, homomorpholin-4-ylcarbonyl-$C_{1-3}$-alkyl, piperazin-1-ylcarbonyl-$C_{1-3}$-alkyl, 4-$C_{1-3}$-alkyl-piperazin-1-ylcarbonyl-$C_{1-3}$-alkyl, homopiperazin-1-ylcarbonyl-$C_{1-3}$-alkyl or a 4-$C_{1-3}$-alkyl-homopiperazin-1-ylcarbonyl-$C_{1-3}$-alkyl group,
  a hydroxy-$C_{2-4}$-alkyl, $C_{1-3}$-alkyloxy-$C_{2-4}$-alkyl, $C_{1-4}$-alkyloxy-carbonylamino-$C_{2-4}$-alkyl, amino-$C_{2-4}$-alkyl, $C_{1-3}$-alkylamino-$C_{2-4}$-alkyl, di-($C_{1-3}$-alkyl)amino-$C_{2-4}$-alkyl, $C_{1-3}$-alkylcarbonylamino-$C_{2-4}$-alkyl, aminocarbonylamino-$C_{2-4}$-alkyl, $C_{1-3}$-alkylaminocarbonylamino-$C_{2-4}$-alkyl, di-($C_{1-3}$-alkyl)amino-carbonylamino-$C_{2-4}$-alkyl, pyrrolidin-1-ylcarbonylamino-$C_{2-4}$-alkyl, piperidin-1-ylcarbonylamino-$C_{2-4}$-alkyl, morpholin-4-ylcarbonylamino-$C_{2-4}$-alkyl, $C_{1-3}$-alkylsulphonyl-$C_{2-4}$-alkyl or a $C_{1-3}$-alkylsulphonylamino-$C_{2-4}$-alkyl group, a (2-oxo-pyrrolidin-1-yl)-$C_{2-4}$-alkyl, (2-oxopiperidin-1-yl)-$C_{2-4}$-alkyl, (3-oxo-morpholin-4-yl)-$C_{2-4}$-alkyl, (2-oxo-imidazolidin-1-yl)-$C_{2-4}$-alkyl, (2-oxo-3-$C_{1-3}$-alkyl-imidazolidin-1-yl)-$C_{2-4}$-alkyl, (2-oxo-hexahydro-pyrimidin-1-yl)-$C_{2-4}$-alkyl or a (2-oxo-3-$C_{1-3}$-alkyl-hexahydropyrimidin-1-yl)-$C_{2-4}$-alkyl group, a $C_{1-4}$-alkylsulphonyl, chloro-$C_{1-4}$-alkylsulphonyl, bromo-$C_{1-4}$-alkylsulphonyl, amino-$C_{1-4}$-alkylsulphonyl, $C_{1-3}$-alkylamino-$C_{1-4}$-alkylsulphonyl, di-($C_{1-3}$-alkyl)amino-$C_{1-4}$-alkylsulphonyl, (pyrrolidin-1-yl)-$C_{1-4}$-alkylsulphonyl, (piperidin-1-yl)-$C_{1-4}$-alkylsulphonyl, (homopiperidin-1-yl)-$C_{1-4}$-alkylsulphonyl, (morpholin-4-yl)-$C_{1-4}$-alkylsulphonyl, (homomorpholin-4-yl)-$C_{1-4}$-alkylsulphonyl, (piperazin-1-yl)-$C_{1-4}$-alkylsulphonyl, (4-$C_{1-3}$-alkyl-piperazin-1-yl)-$C_{1-4}$-alkylsulphonyl, (homopiperazin-1-yl)-$C_{1-4}$-alkylsulphonyl or a (4-$C_{1-3}$-alkyl-homopiperazin-1-yl)-$C_{1-4}$-alkylsulphonyl group, a $C_{1-4}$-alkyloxycarbonyl group, a formyl, $C_{1-4}$-alkyl-carbonyl, $C_{1-3}$-alkyloxy-$C_{1-4}$-alkyl-carbonyl, tetrahydrofuranylcarbonyl, tetrahydropyranylcarbonyl, amino-$C_{1-4}$-alkyl-carbonyl, $C_{1-3}$-alkylamino-$C_{1-4}$-alkyl-carbonyl, di-($C_{1-3}$-alkyl)amino-$C_{1-4}$-alkyl-carbonyl, pyrrolidin-1-yl-$C_{1-4}$-alkyl-carbonyl, piperidin-1-yl-$C_{1-4}$-alkyl-carbonyl, (homopiperidin-1-yl)-$C_{1-4}$-alkyl-carbonyl, morpholin-4-yl-$C_{1-4}$-alkyl-carbonyl, (homomorpholin-4-yl)-$C_{1-4}$-alkyl-carbonyl, (piperazin-1-yl)-$C_{1-4}$-alkyl-carbonyl, (4-$C_{1-3}$-alkyl-piperazin-1-yl)-$C_{1-4}$-alkyl-carbonyl, (homopiperazin-1-yl)-$C_{1-4}$-alkyl-carbonyl, (4-$C_{1-3}$-alkyl-homopiperazin-1-yl)-$C_{1-4}$-alkyl-carbonyl or a $C_{1-3}$-alkylsulphonyl-$C_{1-4}$-alkyl-carbonyl group, a cyano, aminocarbonyl, $C_{1-3}$-alkyl-aminocarbonyl, di-($C_{1-3}$-alkyl)amino-carbonyl, ($C_{1-3}$-alkyloxy-$C_{2-4}$-alkyl)aminocarbonyl, N—($C_{1-3}$-alkyl)-N—($C_{1-3}$-alkyloxy-$C_{2-4}$-alkyl)aminocarbonyl, arylaminocarbonyl, pyrrolidin-1-ylcarbonyl, piperidin-1-ylcarbonyl, homopiperidin-1-ylcarbonyl, morpholin-4-ylcarbonyl, homomorpholin-4-ylcarbonyl, 2-oxa-5-aza-bicyclo[2.2.1]hept-5-ylcarbonyl, 3-oxa-8-aza-bicyclo[3.2.1]oct-8-ylcarbonyl, 8-oxa-3-aza-bicyclo[3.2.1]oct-3-ylcarbonyl, piperazin-1-ylcarbonyl, 4-$C_{1-3}$-alkyl-piperazin-1-ylcarbonyl, homopiperazin-1-ylcarbonyl, 4-$C_{1-3}$-alkyl-homopiperazin-1-ylcarbonyl, aminosulphonyl, $C_{1-3}$-alkyl-aminosulphonyl, di-($C_{1-3}$-alkyl)amino-sulphonyl, pyrrolidin-1-ylsulphonyl, piperidin-1-ylsulphonyl, homopiperidin-1-ylsulphonyl, morpholin-4-ylsulphonyl, homomorpholin-4-ylsulphonyl, piperazin-1-ylsulphonyl, 4-$C_{1-3}$-alkyl-piperazin-1-ylsulphonyl, homopiperazin-1-ylsulphonyl or a 4-$C_{1-3}$-alkyl-homopiperazin-1-ylsulphonyl group, a cyclobutyl, cyclopentyl or cyclohexyl group which is substituted in each case by a group $R^6$, where $R^6$ denotes a 2-oxo-pyrrolidin-1-yl, 2-oxopiperidin-1-yl, 3-oxo-morpholin-4-yl, 2-oxo-imidazolidin-1-yl, 2-oxo-3-$C_{1-3}$-alkyl-imidazolidin-1-yl, 2-oxo-hexahydropyrimidin-1-yl or a 2-oxo-3-$C_{1-3}$-alkyl-hexahydropyrimidin-1-yl group, an azetidin-3-yl group which is substituted in the 1 position by the group $R^5$, while $R^5$ is as hereinbefore defined, a pyrrolidin-3-yl group which is substituted in the 1 position by the group $R^5$, while $R^5$ is as hereinbefore defined, a piperidin-3-yl group which is substituted in the 1 position by the group $R^5$, while $R^5$ is as hereinbefore defined, a piperidin-4-yl group which is substituted in the 1 position by the group $R^5$, while $R^5$ is as hereinbefore defined, or a tetrahydrofuran-3-yl, tetrahydropyran-3-yl or tetrahydropyran-4-yl group, $R^d$ denotes a hydrogen atom or a fluorine, chlorine or bromine atom, a hydroxy group, a $C_{1-4}$-alkyloxy group, a methoxy group substituted by 1 to 3 fluorine atoms, an ethyloxy group substituted by 1 to 5 fluorine atoms, a $C_{2-4}$-alkyloxy group which is substituted by a group $R^6$ or $R^7$, while $R^6$ is as hereinbefore defined and $R^7$ denotes a hydroxy, $C_{1-3}$-alkyloxy, $C_{3-6}$-cycloalkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, 2-oxa-5-aza-bicyclo[2.2.1]hept-5-yl, 3-oxa-8-aza-bicyclo[3.2.1]oct-8-yl, 8-oxa-3-aza-bicyclo[3.2.1]oct-3-yl, piperazin-1-yl, 4-$C_{1-3}$-alkyl-piperazin-1-yl, homopiperazin-1-yl or $C_{1-3}$-alkyl-homopiperazin-1-yl group, or a formylamino, $C_{1-4}$-alkylcarbonylamino, $C_{1-3}$-alkyloxy-$C_{1-3}$-alkyl-carbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, piperazin-1-ylcarbonylamino, 4-$C_{1-3}$-alkyl-piperazin-1-ylcarbonylamino, morpholin-4-ylcarbonylamino or a $C_{1-4}$-alkylsulphonylamino group, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a $C_{1-4}$-alkoxy group which is substituted by a pyrrolidinyl, piperidinyl or homopiperidinyl group substituted in the 1 position by the group $R^8$, while $R^8$ denotes a hydrogen atom or a $C_{1-3}$-alkyl group, or a $C_{1-4}$-alkoxy group which is substituted by a morpholinyl group substituted in the 4 position by the group $R^8$, while $R^8$ is as hereinbefore defined, and X denotes a methyne group substituted by a cyano group or a nitrogen atom, and by the aryl groups mentioned in the definition of the above groups is meant in each case a phenyl group which is mono- or disubstituted by $R^9$, while the substituents may be identical or different and $R^9$ denotes a hydrogen atom, a fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group, by the heteroaryl groups mentioned in the definition of the above groups is meant a pyridyl, pyridazinyl, pyrimidinyl or pyrazinyl group, while the abovementioned heteroaryl groups are each mono- or disubstituted by the group $R^9$, while the substituents may be identical or different and $R^9$ is as hereinbefore defined, and the abovementioned pyrrolidinyl, piperidinyl, piperazinyl and morpholinyl groups may be substituted in each case by one or two $C_{1-3}$-alkyl groups, and unless otherwise stated, the abovementioned alkyl groups may be straight-chained or branched,
their tautomers, their stereoisomers, their mixtures and their salts,
or
the use of an EGFR inhibitor of general formula (II)

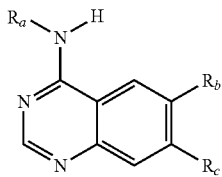
(II)

wherein
$R_a$ denotes a benzyl or 1-phenylethyl group or a phenyl group substituted by the groups $R_1$ and $R_2$, wherein
  $R_1$ denotes a hydrogen, fluorine, chlorine or bromine atom, a methyl, trifluoromethyl, cyano or ethynyl group and
  $R_2$ denotes a hydrogen or fluorine atom,
one of the groups $R_b$ or $R_c$ denotes an $R_3$—$(CH_2)_m$—O group and the other group $R_b$ or $R_c$ denotes a methoxy, cyclobutyloxy, cyclopentyloxy, cyclopropylmethoxy, cyclobutylmethoxy, cyclopentylmethoxy, tetrahydrofuran-3-yloxy, tetrahydropyran-3-yloxy, tetrahydropyran-4-yloxy, tetrahydrofuranylmethoxy or tetrahydropyranylmethoxy group, where
  $R_3$ denotes an N-(2-oxo-tetrahydrofuran-4-yl)-methylamino or N-(2-oxo-tetrahydrofuran-4-yl)-ethylamino group,
  an $R_4$—O—CO—$CH_2$—N—$CH_2CH_2$—OH group substituted at the methylene groups by one or two methyl or ethyl groups, wherein
    $R_4$ represents a hydrogen atom or a $C_{1-4}$-alkyl group,
  or a 2-oxo-morpholin-4-yl group substituted by one or two methyl or ethyl groups and
  m denotes the number 2, 3 or 4,
the tautomers, the stereoisomers and the salts thereof,
or
the use of an EGFR inhibitor of general formula (III)

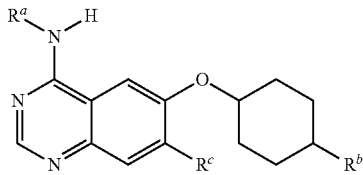
(III)

wherein
$R^a$ denotes a phenyl, 1-phenylethyl or indan-4-yl group, wherein the phenyl nucleus is substituted in each case by the groups $R^1$ to $R^3$, wherein
  $R^1$ and $R^2$, which may be identical or different, each denote a hydrogen, fluorine, chlorine, bromine or iodine atom,
    a $C_{1-4}$-alkyl, hydroxy, $C_{1-4}$-alkoxy, $C_{2-3}$-alkenyl or $C_{2-3}$-alkynyl group,
    an aryl, aryloxy, arylmethyl or arylmethoxy group,
    a heteroaryl, heteroaryloxy, heteroarylmethyl or heteroarylmethoxy group,
    a methyl or methoxy group substituted by 1 to 3 fluorine atoms or
    a cyano, nitro or amino group, and
  $R^3$ denotes a hydrogen, fluorine, chlorine or bromine atom or
    a methyl or trifluoromethyl group,
$R^b$ denotes an azetidin-1-yl, pyrrolidin-1-yl, piperidin-1-yl, homopiperidin-1-yl, morpholin-4-yl, homomorpholin-4-yl, piperazin-1-yl, 4-($C_{1-4}$-alkyl-carbonyl)-piperazin-1-yl, 4-($C_{1-4}$-alkyl-sulphonyl)-piperazin-1-yl, homopiperazin-1-yl, 4-($C_{1-4}$-alkyl-carbonyl)-homopiperazin-1-yl or 4-($C_{1-4}$-alkyl-sulphonyl)-homopiperazin-1-yl group which may be mono-, di- or trisubstituted by $R^4$ in each case, while the substituents may be identical or different and
  $R^4$ denotes a fluorine, chlorine, bromine or iodine atom,
    a $C_{1-4}$-alkyl, $C_{2-4}$-alkenyl or $C_{2-4}$-alkynyl group,
    a methyl or methoxy group substituted by 1 to 3 fluorine atoms,
    an amino, $C_{1-4}$-alkylamino, di-($C_{1-4}$-alkyl)amino, $C_{1-4}$-alkyl-carbonylamino, N—($C_{1-4}$-alkyl)-$C_{1-4}$-alkyl-carbonylamino, $C_{1-4}$-alkyl-sulphonylamino or N—($C_{1-4}$-alkyl)-$C_{1-4}$-alkyl-sulphonylamino group,
    an amino-$C_{1-4}$-alkyl, $C_{1-4}$-alkylamino-$C_{1-4}$-alkyl, di-($C_{1-4}$-alkyl)amino-$C_{1-4}$-alkyl, $C_{1-4}$-alkyl-carbonylamino-$C_{1-4}$-alkyl, N—($C_{1-4}$-alkyl)-$C_{1-4}$-alkyl-carbonylamino-$C_{1-4}$-alkyl, $C_{1-4}$-alkyl-sulphonylamino-$C_{1-4}$-alkyl or N—($C_{1-4}$-alkyl)-$C_{1-4}$-alkyl-sulphonylamino-$C_{1-4}$-alkyl group,
    a hydroxy, $C_{1-4}$-alkyloxy or $C_{1-4}$-alkyl-carbonyloxy group
    a hydroxy-$C_{1-4}$-alkyl, $C_{1-4}$-alkyloxy-$C_{1-4}$-alkyl or $C_{1-4}$-alkyl-carbonyloxy-$C_{1-4}$-alkyl group,
    a $C_{1-4}$-alkyl-carbonyl, cyano, $C_{1-4}$-alkyl-oxycarbonyl, carboxy, aminocarbonyl,
    $C_{1-4}$-alkyl-aminocarbonyl, di-($C_{1-4}$-alkyl)amino-carbonyl, pyrrolidin-1-yl-carbonyl, piperidin-1-yl-carbonyl, piperazin-1-yl-carbonyl, 4-$C_{1-4}$-alkyl-piperazin-1-yl-carbonyl or morpholin-4-yl-carbonyl group,
    a $C_{1-4}$-alkylcarbonyl-$C_{1-4}$-alkyl, cyano-$C_{1-4}$-alkyl, $C_{1-4}$-alkyloxycarbonyl-$C_{1-4}$-alkyl, aminocarbonyl-$C_{1-4}$-alkyl, $C_{1-4}$-alkylaminocarbonyl-$C_{1-4}$-alkyl, di-($C_{1-4}$-alkyl)aminocarbonyl-$C_{1-4}$-alkyl, pyrrolidin-1-yl-carbonyl-$C_{1-4}$-alkyl, piperidin-1-yl-carbonyl-$C_{1-4}$-alkyl, piperazin-1-yl-carbonyl-$C_{1-4}$-alkyl, 4-$C_{1-4}$-alkyl-piperazin-1-yl-carbonyl-$C_{1-4}$-alkyl or morpholin-4-yl-carbonyl-$C_{1-4}$-alkyl group,
    a $C_{1-4}$-alkylsulphanyl, $C_{1-4}$-alkylsulphinyl, $C_{1-4}$-alkylsulphonyl, aminosulphonyl, $C_{1-4}$-alkyl-aminosulphonyl or di-($C_{1-4}$-alkyl)amino-sulphonyl group,
    a $C_{1-4}$-alkylsulphanyl-$C_{1-4}$-alkyl, $C_{1-4}$-alkylsulphinyl-$C_{1-4}$-alkyl, $C_{1-4}$-alkylsulphonyl-$C_{1-4}$-alkyl, aminosulphonyl-$C_{1-4}$-alkyl, $C_{1-4}$-alkyl-aminosulphonyl-$C_{1-4}$-alkyl or di-($C_{1-4}$-alkyl)amino-sulphonyl-$C_{1-4}$-alkyl group
    and wherein the heterocycles mentioned under $R^b$ above may additionally be substituted by an oxo group,
$R^c$ denotes a hydrogen atom,
  a fluorine, chlorine, bromine or iodine atom,
  a $C_{1-4}$-alkyl group,
  a $C_{1-4}$-alkyl group which is substituted by an $R^5$ group, where
    $R^5$ denotes a hydroxy, $C_{1-3}$-alkyloxy, $C_{3-6}$-cycloalkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, 2-oxa-5-aza-bicyclo[2,2,1]hept-5-yl, 3-oxa-8-aza-bicyclo[3.2.1]oct-8-yl, 8-oxa-3-aza-bicyclo[3.2.1]oct-3-yl, piperazin-1-yl, 4-$C_{1-3}$-alkyl-piperazin-1-yl, homopiperazin-1-yl or $C_{1-3}$-alkyl-homopiperazin-1-yl group or a formylamino, $C_{1-4}$-alkylcarbonylamino, $C_{1-3}$-alkyloxy-$C_{1-3}$-alkyl-carbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, piperazin-1-ylcarbonylamino, 4-$C_{1-3}$-alkyl-piperazin-1-ylcarbonylamino, morpholin-4-ylcarbonylamino or a $C_{1-4}$-alkylsulphonylamino group, a hydroxy group, a $C_{1-4}$-alkyloxy group, a methoxy or ethyloxy group substituted by 1 to 3 fluorine atoms, a $C_{2-4}$-alkyloxy group which is substituted by the group $R^5$, where $R^5$ is as hereinbefore defined, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a $C_{1-4}$-alkoxy group which is substituted by a pyrrolidinyl, piperidinyl or homopiperidinyl group substituted in the 1 position by the group $R^6$, where $R^6$ denotes a hydrogen atom or a $C_{1-3}$-alkyl group, or a $C_{1-4}$-alkoxy group which is substituted by a morpholinyl group substituted in the 4 position by the group $R^6$, where $R^6$ is as hereinbefore defined, and wherein the pyrrolidinyl, piperidinyl, piperazinyl and morpholinyl groups mentioned above in the definition of the group $R^c$ may each be substituted by one or two $C_{1-3}$-alkyl groups, and wherein by the aryl groups mentioned in the definition of the foregoing groups is meant in each case a phenyl group which is mono- or disubstituted by $R^7$, wherein the substituents may be identical or different and $R^7$ denotes a hydrogen atom, a fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group, and by the heteroaryl groups mentioned in the definition of the foregoing groups is meant a pyridyl, pyridazinyl, pyrimidinyl or pyrazinyl group, wherein the above-mentioned heteroaryl groups are mono- or disubstituted by the group $R^7$, wherein the substituents may be identical or different and $R^7$ is as hereinbefore defined, and unless stated otherwise, the above-mentioned alkyl groups may be straight-chain or branched, the tautomers, the stereoisomers, the mixtures thereof and salts thereof, or the use of an EGFR inhibitor of general formula (IV)
Compounds of General Formula (I)

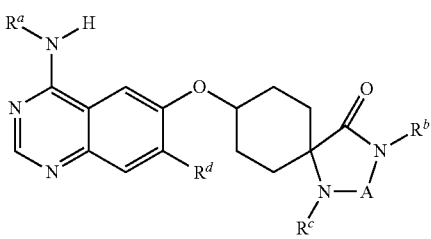

(I)

characterised in that $R^a$ denotes a phenyl or 1-phenylethyl group, wherein the phenyl nucleus is substituted in each case by the groups $R^1$ to $R^3$, wherein $R^1$ and $R^2$ which may be identical or different, denote hydrogen or a group selected from among
F, Cl, Br, I, $OCH_2F$, $OCHF_2$, $OCF_3$, $CH_2F$, $CHF_2$, $CF_3$, CN, $NO_2$, $NH_2$ and OH, or a group selected from among
$C_{1-4}$-alkyl, $C_{1-4}$-alkyl-O, $C_{2-3}$-alkenyl, $C_{2-3}$-alkynyl, phenyl, phenyl-O, phenyl-$C_{1-3}$-alkyl, phenyl-$C_{1-3}$-alkyl-O, heteroaryl, heteroaryl-O, heteroaryl-$C_{1-3}$-alkyl, heteroaryl-$C_{1-3}$-alkyl-O, while the above-mentioned phenyl groups are mono- or disubstituted by groups $R^5$, and $R^3$ denotes hydrogen, or a group selected from among
F, Cl, Br and $CH_3$, $R^b$ denotes hydrogen, or a group, optionally substituted, selected from among $C_{1-6}$-alkyl, $C_{3-6}$-cycloalkyl- and $C_{3-6}$-cycloalkyl-$C_{1-3}$-alkyl, $R^c$ denotes hydrogen, or an optionally substituted group selected from among $C_{1-6}$-alkyl, $C_{3-6}$-cycloalkyl, $C_{3-6}$-cycloalkyl-$C_{1-3}$-alkyl, $C_{1-6}$-alkyl-CO, $C_{3-6}$-cycloalkyl-CO, $C_{3-6}$-cycloalkyl-$C_{1-3}$-alkyl-CO, $C_{1-6}$-alkyl-$SO_2$, $C_{3-6}$-cycloalkyl-$SO_2$, $C_{3-6}$-cycloalkyl-$C_{1-3}$-alkyl-$SO_2$, phenyl-CO— and phenyl-$SO_2$, $R^d$ denotes hydrogen or a group selected from among
F, Cl, Br, I, OH, $C_{1-4}$-alkyl, $C_{1-4}$-alkyl-O, $C_{1-2}$-alkyl-O substituted by 1 to 3 fluorine atoms, $C_{3-7}$-cycloalkyl-O, $C_{3-7}$-cycloalkyl-$C_{1-4}$-alkyl-O, tetrahydrofuran-3-yl-O, tetrahydropyran-3-yl-O, tetrahydro-pyran-4-yl-O, tetrahydrofuranyl-$C_{1-4}$-alkyl-O— and tetrahydropyranyl-$C_{1-4}$-alkyl-O, or $R^4$—$C_{1-4}$-alkyl, while the linking of the groups $R^4$ may take place via each C atom of the alkyl group, or $R^4$—$C_{2-4}$-alkyl-O, wherein the group $R^4$ is separated from the oxygen atom by at least 2 C atoms, or a group selected from among
pyrrolidin-2-yl-$C_{1-4}$-alkyl-O, pyrrolidin-3-yl-$C_{1-4}$-alkyl-O, piperidin-2-yl-$C_{1-4}$-alkyl-O, piperidin-3-yl-$C_{1-4}$-alkyl-O, piperidin-4-yl-$C_{1-4}$-alkyl-O, azepan-2-yl-$C_{1-4}$-alkyl-O, azepan-3-yl-$C_{1-4}$-alkyl-O, azepan-4-yl-$C_{1-4}$-alkyl-O, morpholin-2-yl-$C_{1-4}$-alkyl-O, morpholin-3-yl-$C_{1-4}$-alkyl-O, 1-($C_{1-3}$-alkyl)-pyrrolidin-2-yl-$C_{1-4}$-alkyl-O, 1-($C_{1-3}$-alkyl)-pyrrolidin-3-yl-$C_{1-4}$-alkyl-O, 1-($C_{1-3}$-alkyl)-piperidin-2-yl-$C_{1-4}$-alkyl-O, 1-($C_{1-3}$-alkyl)-piperidin-3-yl-$C_{1-4}$-alkyl-O, 1-($C_{1-3}$-alkyl)-piperidin-4-yl-$C_{1-4}$-alkyl-O, 1-($C_{1-3}$-alkyl)-azepan-2-yl-$C_{1-4}$-alkyl-O, 1-($C_{1-3}$-alkyl)-azepan-3-yl-$C_{1-4}$-alkyl-O, 1-($C_{1-3}$-alkyl)-azepan-4-yl-$C_{1-4}$-alkyl-O, 4-($C_{1-3}$-alkyl)-morpholin-2-yl-$C_{1-4}$-alkyl-O— and 4-($C_{1-3}$-alkyl)-morpholin-3-yl-$C_{1-4}$-alkyl-O, while $R^4$ denotes a group, which may be identical or different, selected from among
OH, $C_{1-3}$-alkyl-O, $C_{3-6}$-cycloalkyl-O, $NH_2$, $C_{1-3}$-alkyl-NH, ($C_{1-3}$-alkyl)$_2$N, (2-methoxyethyl)$_2$N, pyrrolidin-1-yl, piperidin-1-yl, azepan-1-yl, morpholin-4-yl, 1,4-oxazepan-4-yl, 2-oxa-5-aza-bicyclo[2,2,1]hept-5-yl, 3-oxa-8-aza-bicyclo[3.2.1]oct-8-yl, 8-oxa-3-aza-bicyclo[3.2.1]oct-3-yl, piperazin-1-yl, 4-($C_{1-3}$-alkyl)-piperazin-1-yl, 1,4-diazepan-1-yl, 4-($C_{1-3}$- alkyl)-1,4-diazepan-1-yl, HCO—NH, $C_{1-4}$-alkyl-CO—NH, $C_{1-3}$-alkyl-O—$C_{1-3}$-alkyl-CO—NH, $C_{1-4}$-alkyl-O—CO—NH, $H_2NCONH$, $C_{1-3}$-alkyl-NH—CO—NH, $(C_{1-3}$-alkyl)$_2$N—CONH, pyrrolidin-1-yl-CO—NH, piperidin-1-yl-CO—NH, piperazin-1-yl-CO—NH, 4-($C_{1-3}$-alkyl)-piperazin-1-yl-CO—NH, morpholin-4-yl-CO—NH— and $C_{1-4}$-alkyl-SO$_2$—NH, while the pyrrolidinyl, piperidinyl, azepan-1-yl, piperazinyl, 1,4-diazepan-1-yl, morpholinyl- and 1,4-oxazepan-4-yl groups mentioned above in the definition of the group $R^d$ may each additionally be substituted by one or two $C_{1-3}$-alkyl groups, and wherein the above-mentioned phenyl groups are mono- or disubstituted by groups $R^5$, wherein $R^5$ denotes hydrogen, or a group, which may be identical or different, selected from among F, Cl, Br, I, OH, CN, $C_{1-3}$-alkyl, $C_{1-3}$-alkyl-O, $CHF_2$, $CF_3$, —O—$CHF_2$ and —O—$CF_3$, and unless stated otherwise, the above-mentioned alkyl groups may be straight-chain or to branched, A denotes —CO or —$C_1$-$C_3$-alkylene, while the —$C_1$-$C_3$-alkylene-group may be 1-, 2-, 3- or 4-substituted by a group $R^6$, and $R^6$ which may be identical or different, denotes hydrogen, or a group selected from among OH, $C_1$-$C_4$-alkyl and —O—$C_1$-$C_4$-alkyl optionally in the form of the tautomers, the racemates, the enantiomers, the diastereomers and the mixtures thereof, and optionally the pharmacologically acceptable acid addition salts, solvates and hydrates thereof.

for the manufacture of a medicament for the treatment of virus-induced diseases.

The invention also provides the use of an EGFR inhibitor selected from a group consisting of (1.1) 4-[(3-chloro-4-fluoro-phenyl)amino]-6-[2-((S)-6-methyl-2-oxo-morpholin-4-yl)-ethoxy]-7-methoxy-quinazoline, (1.2) 4-[(3-chloro-4-fluoro-phenyl)amino]-6-[2-(2,2-dimethyl-6-oxo-morpholin-4-yl)-ethoxy]-7-methoxy-quinazoline, (1.3) 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, (1.4) 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, (1.5) 4-[(3-chloro-4-fluoro-phenyl)amino]-6-[1-(tert.-butyloxycarbonyl)-piperidin-4-yloxy]-7-methoxy-quinazoline, (1.6) 4-[(3-chloro-4-fluoro-phenyl)amino]-6-(trans-4-amino-cyclohexan-1-yloxy)-7-methoxy-quinazoline, (1.7) 4-[(3-chloro-4-fluoro-phenyl)amino]-6-(trans-4-methansulfonylamino-cyclohexan-1-yloxy)-7-methoxy-quinazoline, (1.8) 4-[(3-chloro-4-fluoro-phenyl)amino]-6-(tetrahydropyran-3-yloxy)-7-methoxy-quinazoline, (1.9) 4-[(3-chloro-4-fluoro-phenyl)amino]-6-(1-methyl-piperidin-4-yloxy)-7-methoxy-quinazoline, (1.10) 4-[(3-chloro-4-fluoro-phenyl)amino]-6-{1-[(morpholin-4-yl)carbonyl]-piperidin-4-yloxy}-7-methoxy-quinazoline, (1.11) 4-[(3-chloro-4-fluoro-phenyl)amino]-6-{1-[(methoxymethyl)carbonyl]-piperidin-4-yloxy}-7-methoxy-quinazoline, (1.12) 4-[(3-chloro-4-fluoro-phenyl)amino]-6-(piperidin-3-yloxy)-7-methoxy-quinazoline, (1.13) 4-[(3-chloro-4-fluoro-phenyl)amino]-6-[1-(2-acetylamino-ethyl)-piperidin-4-yloxy]-7-methoxy-quinazoline, (1.14) 4-[(3-chloro-4-fluoro-phenyl)amino]-6-(tetrahydropyran-4-yloxy)-7-ethoxy-quinazoline (1.15) 4-[(3-chloro-4-fluoro-phenyl)amino]-6-((S)-tetrahydrofuran-3-yloxy)-7-hydroxy-quinazoline, (1.16) 4-[(3-chloro-4-fluoro-phenyl)amino]-6-(tetrahydropyran-4-yloxy)-7-(2-methoxy-ethoxy)-quinazoline, (1.17) 4-[(3-chloro-4-fluoro-phenyl)amino]-6-{trans-4-[(dimethylamino)sulfonylamino]-cyclohexan-1-yloxy}-7-methoxy-quinazoline, (1.18) 4-[(3-chloro-4-fluoro-phenyl)amino]-6-{trans-4-[(morpholin-4-yl)carbonylamino]-cyclohexan-1-yloxy}-7-methoxy-quinazoline, (1.19) 4-[(3-chloro-4-fluoro-phenyl)amino]-6-{trans-4-[(morpholin-4-yl)sulfonylamino]-cyclohexan-1-yloxy}-7-methoxy-quinazoline, (1.20) 4-[(3-chloro-4-fluoro-phenyl)amino]-6-(tetrahydropyran-4-yloxy)-7-(2-acetylamino-ethoxy)-quinazoline, (1.21) 4-[(3-chloro-4-fluoro-phenyl)amino]-6-(tetrahydropyran-4-yloxy)-7-(2-methan-sulfonylamino-ethoxy)-quinazoline, (1.22) 4-[(3-chloro-4-fluoro-phenyl)amino]-6-{1-[(piperidin-1-yl)carbonyl]-piperidin-4-yloxy}-7-methoxy-quinazoline, (1.23) 4-[(3-chloro-4-fluoro-phenyl)amino]-6-(1-aminocarbonylmethyl-piperidin-4-yloxy)-7-methoxy-quinazoline, (1.24) 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, (1.25) 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, (1.26) 4-[(3-chloro-4-fluoro-phenyl)amino]-6-(cis-4-{N-[(morpholin-4-yl)sulfonyl]-N-methyl-amino}-cyclohexan-1-yloxy)-7-methoxy-quinazoline, (1.27) 4-[(3-chloro-4-fluoro-phenyl)amino]-6-(trans-4-ethansulfonylamino-cyclohexan-1-yloxy)-7-methoxy-quinazoline, (1.28) 4-[(3-chloro-4-fluoro-phenyl)amino]-6-(1-methansulfonyl-piperidin-4-yloxy)-7-ethoxy-quinazoline, (1.29) 4-[(3-chloro-4-fluoro-phenyl)amino]-6-(1-methansulfonyl-piperidin-4-yloxy)-7-(2-methoxy-ethoxy)-quinazoline, (1.30) 4-[(3-chloro-4-fluoro-phenyl)amino]-6-[1-(2-methoxy-acetyl)-piperidin-4-yloxy]-7-(2-methoxy-ethoxy)-quinazoline, (1.31) 4-[(3-chloro-4-fluoro-phenyl)amino]-6-(cis-4-acetylamino-cyclohexan-1-yloxy)-7-methoxy-quinazoline, (1.32) 4-[(3-ethinyl-phenyl)amino]-6-[1-(tert.-butyloxycarbonyl)-piperidin-4-yloxy]-7-methoxy-quinazoline, (1.33) 4-[(3-ethinyl-phenyl)amino]-6-(tetrahydropyran-4-yloxy]-7-methoxy-quinazoline, (1.34) 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, (1.35) 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, (1.36) 4-[(3-chloro-4-fluoro-phenyl)amino]-6-{cis-4-[(morpholin-4-yl)carbonylamino]-cyclohexan-1-yloxy}-7-methoxy-quinazoline, (1.37) 4-[(3-chloro-4-fluoro-phenyl)amino]-6-{1-[2-(2-oxopyrrolidin-1-yl)ethyl]-piperidin-4-yloxy}-7-methoxy-quinazoline, (1.38) 4-[(3-chloro-4-fluoro-phenyl)amino]-6-{1-[(morpholin-4-yl)carbonyl]-piperidin-4-yloxy}-7-(2-methoxy-ethoxy)-quinazoline, (1.39) 4-[(3-ethinyl-phenyl)amino]-6-(1-acetyl-piperidin-4-yloxy)-7-methoxy-quinazoline, (1.40) 4-[(3-ethinyl-phenyl)amino]-6-(1-methyl-piperidin-4-yloxy)-7-methoxy-quinazoline, (1.41) 4-[(3-ethinyl-phenyl)amino]-6-(1-methansulfonyl-piperidin-4-yloxy)-7-methoxy-quinazoline, (1.42) 4-[(3-chloro-4-fluoro-phenyl)amino]-6-(1-methyl-piperidin-4-yloxy)-7(2-methoxy-ethoxy)-quinazoline, (1.43) 4-[(3-chloro-4-fluoro-phenyl)amino]-6-(1-isopropyloxycarbonyl-piperidin-4-yloxy)-7-methoxy-quinazoline, (1.44) 4-[(3-chloro-4-fluoro-phenyl)amino]-6-(cis-4-methylamino-cyclohexan-1-yloxy)-7-methoxy-quinazoline, (1.45) 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, (1.46) 4-[(3-ethinyl-phenyl)amino]-6-(piperidin-4-yloxy)-7-methoxy-quinazoline, (1.47) 4-[(3-ethinyl-phenyl)amino]-6-[1-(2-methoxy-acetyl)-piperidin-4-yloxy]-7-methoxy-quinazoline, (1.48) 4-[(3-ethinyl-phenyl)amino]-6-{1-[(morpholin-4-yl)carbonyl]-piperidin-4-yloxy}-7-methoxy-quinazoline, (1.49) 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, (1.50) 4-[(3-chloro-4-fluoro-phenyl)amino]-6-{1-[(2-methyl-morpholin-4-yl)carbonyl]-piperidin-4-yloxy}-7-methoxy-quinazoline, (1.51) 4-[(3-chloro-4-fluoro-phenyl)amino]-6-{1-[(S,S)-(2-oxa-5-aza-bicyclo[2.2.1]hept5-yl)carbonyl]-piperidin-4-yloxy}-7-methoxy-quinazoline, (1.52) 4-[(3-chloro-4-fluoro-phenyl)amino]-6-{1-[(N-methyl-N-2-methoxyethyl-amino)carbonyl]-piperidin-4-yloxy}-7-methoxy-quinazoline, (1.53) 4-[(3-chloro-4-fluoro-phenyl)amino]-6-(1-ethyl-piperidin-4-yloxy)-7-methoxy-quinazoline, (1.54) 4-[(3-chloro-4-fluoro-phenyl)amino]-6-{1-[(2-methoxyethyl)carbonyl]-piperidin-4-yloxy}-7-methoxy-quinazoline, (1.55) 4-[(3-chloro-4-fluoro-phenyl)amino]-6-{1-[(3-methoxypropyl-amino)-carbonyl]-piperidin-4-yloxy}-7-methoxy-quinazoline, (1.56) 4-[(3-chloro-4-fluoro-phenyl)amino]-6-[cis-4-(N-methansulfonyl-N-methyl-amino)-cyclohexan-1-yloxy]-7-methoxy-quinazoline, (1.57) 4-[(3-chloro-4-fluoro-phenyl)amino]-6-[cis-4-(N-acetyl-N-methyl-amino)-cyclohexan-1-yloxy]-7-methoxy-quinazoline, (1.58) 4-[(3-chloro-4-fluoro-phenyl)amino]-6-(trans-4-methylamino-cyclohexan-1-yloxy)-7-methoxy-quinazoline, (1.59) 4-[(3-chloro-4-fluoro-phenyl)amino]-6-[trans-4-(N-methansulfonyl-N-methyl-amino)-cyclohexan-1-yloxy]-7-methoxy-quinazoline, (1.60) 4-[(3-chloro-4-fluoro-phenyl)amino]-6-(trans-4-dimethylamino-cyclohexan-1-yloxy)-7-methoxy-quinazoline, (1.61) 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, (1.62) 4-[(3-chloro-4-fluoro-phenyl)amino]-6-{1-[2-(2-oxo-3-methyl-imidazolidin-1-yl)ethyl]-piperidin-4-yloxy}-7-methoxy-quinazoline, (1.63) 4-[(3-chloro-4-fluoro-phenyl)amino]-6-{1-[2-(2-oxo-hexahydropyrimidin-1-yl)ethyl]-piperidin-4-yloxy}-7-methoxy-quinazoline, (1.64) 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, (1.65) 4-[(3-chloro-4-fluoro-phenyl)amino]-6-(1-methansulfonyl-piperidin-4-yloxy)-7-methoxy-quinazoline, (1.66) 4-[(3-chloro-4-fluoro-phenyl)amino]-6-(1-cyano-piperidin-4-yloxy)-7-methoxy-quinazoline, (1.67) 4-[(3-chloro-4-fluoro-phenyl)amino]-6-(tetrahydropyran-4-yloxy)-7-methoxy-quinazoline, (1.68) 4-[(3-chloro-4-fluoro-phenyl)amino]-6-(1-methylcarbonyl-piperidin-4-yloxy)-7-methoxy-quinazoline, (1.69) 4-[(3-chloro-4-fluoro-phenyl)amino]-6-(1-dimethylaminoacetyl-piperidin-4-yloxy)-7-methoxy-quinazoline, (1.70) 4-[(3-chloro-4-fluoro-phenyl)amino]-6-{1-[(dimethylamino)carbonylmethyl]-piperidin-4-yloxy}-7-methoxy-quinazoline, (1.71) 4-[(3-chloro-4-fluoro-phenyl)amino]-6-(1-methansulfonyl-piperidin-4-yloxy)-quinazoline, (1.72) 4-[(3-chloro-2-fluoro-phenyl)amino]-6-[cis-4-(morpholin-4-yl)-cyclohexyloxy]-7-methoxy-quinazoline, (1.73) 4-[(3-chloro-2-fluoro-phenyl)amino]-6-[trans-4-(morpholin-4-yl)-cyclohexyloxy]-7-methoxy-quinazoline, (1.74) 4-[(3-chloro-2-fluoro-phenyl)amino]-6-[(R)-cis-4-(3-hydroxy-pyrrolidin-1-yl)-cyclohexyloxy]-7-methoxy-quinazoline, (1.75) 4-[(3-chloro-2-fluoro-phenyl)amino]-6-[(R)-trans-4-(3-hydroxy-pyrrolidin-1-yl)-cyclohexyloxy]-7-methoxy-quinazoline, (1.76) 4-[(3-chloro-2-fluoro-phenyl)amino]-6-[cis-4-(3-oxo-piperazin-1-yl)-cyclohexyloxy]-7-methoxy-quinazoline, (1.77) 4-[(3-chloro-2-fluoro-phenyl)amino]-6-[trans-4-(3-oxo-piperazin-1-yl)-cyclohexyloxy]-7-methoxy-quinazoline, (1.78) 4-[(3-chloro-2-fluoro-phenyl)amino]-6-[(S)-cis-4-(3-hydroxy-pyrrolidin-1-yl)-cyclohexyloxy]-7-methoxy-quinazoline, (1.79) 4-[(3-chloro-2-fluoro-phenyl)amino]-6-[(S)-trans-4-(3-hydroxy-pyrrolidin-1-yl)-cyclohexyloxy]-7-methoxy-quinazoline, (1.80) 4-[(3-chloro-2-fluoro-phenyl)amino]-6-{(S)-cis-4-[2-(aminocarbonyl)-pyrrolidin-1-yl]-cyclohexyloxy}-7-methoxy-quinazoline, (1.81) 4-[(3-chloro-2-fluoro-phenyl)amino]-6-{(S)-trans-4-[2-(aminocarbonyl)-pyrrolidin-1-yl]-cyclohexyloxy}-7-methoxy-quinazoline, (1.82) 4-[(3-chloro-2-fluoro-phenyl)amino]-6-[cis-4-(4-hydroxy-piperidin-1-yl)-cyclohexyloxy]-7-methoxy-quinazoline, (1.83) 4-[(3-chloro-2-fluoro-phenyl)amino]-6-[trans-4-(4-hydroxy-piperidin-1-yl)-cyclohexyloxy]-7-methoxy-quinazoline, (1.84) 4-[(3-chloro-2-fluoro-phenyl)amino]-6-[cis-4-(4-methyl-3-oxo-piperazin-1-yl)-cyclohexyloxy]-7-methoxy-quinazoline, and (1.85) 4-[(3-chloro-2-fluoro-phenyl)amino]-6-[trans-4-(4-methyl-3-oxo-piperazin-1-yl)-cyclohexyloxy]-7-methoxy-quinazoline, (1.86) anti-9-[4-(3-chloro-2-fluoro-phenylamino)-7-methoxy-quinazolin-6-yloxy]-1,4-diaza-spiro[5.5]undecan-5-one
(1.87) syn-9-[4-(3-chloro-2-fluoro-phenylamino)-7-methoxy-quinazolin-6-yloxy]-1,4-diaza-spiro[5.5]undecan-5-one
(1.88) anti-9-[4-(3-chloro-2-fluoro-phenylamino)-7-methoxy-quinazolin-6-yloxy]-1-methyl-1,4-diaza-spiro[5.5]undecan-5-one
(1.89) anti-9-[4-(3-chloro-2-fluoro-phenylamino)-7-methoxy-quinazolin-6-yloxy]-1,4-dimethyl-1,4-diaza-spiro[5.5]undecan-5-one
(1.90) anti-8-[4-(3-chloro-2-fluoro-phenylamino)-7-methoxy-quinazolin-6-yloxy]-1,3-diaza-spiro[4.5]decan-2,4-dione
(1.91) syn-8-[4-(3-chloro-2-fluoro-phenylamino)-7-methoxy-quinazolin-6-yloxy]-1,3-diaza-spiro[4.5]decan-2,4-dione optionally in the form of tautomers, racemates, enantiomers, diastereomers, pharmacologically acceptable acid addition salts, solvates or hydrates thereof, for the manufacture of a medicament for the treatment of virus-induced diseases.

Preferably the present invention relates to the said use wherein the virus-induced disease is a respiratory disease.

Further preferred is the use of therapeutically effective amounts of the compounds for the treatment of virus-induced exacerbation of a respiratory disease.

Further preferred is the said use, wherein the respiratory disease is selected from the group consisting of asthma, chronic obstructive pulmonary disease (COPD), chronic bronchitis, otitis media, sinusitis, pneumonia, lung fibrosis and cystic fibrosis, preferably asthma, chronic obstructive pulmonary disease (COPD) and chronic bronchitis, most preferably COPD.

Further preferred is said use, wherein the treatment is by airway delivery.

Further preferred is said use, wherein said treatment is by oral delivery.

Further preferred is said use, wherein said virus is selected from the group consisting of Rhinovirus, influenza virus, parainfluenza virus, coronavirus, adenovirus, respiratory syncytial virus, picornavirus, metapneumovirus, hantavirus, measles virus, Epstein-Barr virus, herpes simplex virus, cytomegalovirus, Rhinovirus, influenza virus, parainfluenza virus, coronavirus, adenovirus, respiratory syncytial virus, picornavirus and metapneumovirus, preferably influenza virus, rhinovirus, respiratory syncytial virus, adenovirus, parainfluenza virus, corona virus, picornavirus and metapneumovirus, more preferably influenza virus, rhinovirus, respiratory syncytial virus, adenovirus and parainfluenza virus, most preferably influenza virus, rhinovirus and respiratory syncytial virus.

The EGFR inhibitors (1.1) to (1.85) can be administered in combination with one or more active agents, e.g. other EGFR inhibitors, antibiotics, antiviral agents, beta-2 mimetics, steroids, PDE-IV inhibitors, p38 MAP kinase inhibitors, $NK_1$ antagonists, anticholinergics and endothelin antagonists.

The EGFR inhibitors will be preferentially administered once or twice daily in a dose range of 0.001-10 mg, when administered via inhalation or in a dose range of 0.5-100 mg when administered via the oral route

The invention claimed is:
1. A method for the treatment of viral infection and exacerbation in respiratory diseases comprising administering to a patient in need thereof a therapeutically effective amount of a compound of formula (IV)

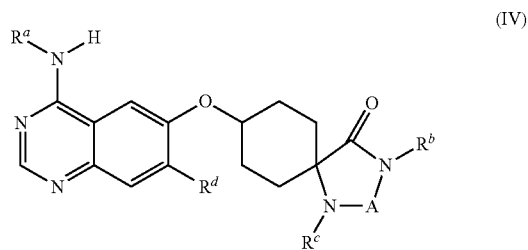

wherein:
$R^a$ denotes a phenyl or 1-phenylethyl group, wherein the phenyl nucleus is substituted in each case by the groups $R^1$ to $R^3$, wherein
$R^1$ and $R^2$ which may be identical or different, denote hydrogen or a group selected from among
F, Cl, Br, I, $OCH_2F$, $OCHF_2$, $OCF_3$, $CH_2F$, $CHF_2$, $CF_3$, CN, $NO_2$, $NH_2$ and OH,
or
a group selected from among
$C_{1-4}$-alkyl, $C_{1-4}$-alkyl-O, $C_{2-3}$-alkenyl, $C_{2-3}$-alkynyl, phenyl, phenyl-O, phenyl-$C_{1-3}$-alkyl, phenyl-$C_{1-3}$-alkyl-O, heteroaryl, heteroaryl-O, heteroaryl-$C_{1-3}$-alkyl, heteroaryl-$C_{1-3}$-alkyl-O, while the above-mentioned phenyl groups are mono- or disubstituted by groups $R^5$,
and
$R^3$ denotes hydrogen,
or
a group selected from among
F, Cl, Br and $CH_3$,
$R^b$ denotes hydrogen, or a group, optionally substituted, selected from among $C_{1-6}$-alkyl, $C_{3-6}$-cycloalkyl- and $C_{3-6}$-cycloalkyl-$C_{1-3}$-alkyl,
$R^c$ denotes hydrogen, or an optionally substituted group selected from among $C_{1-6}$-alkyl, $C_{3-6}$-cycloalkyl, $C_{3-6}$-cycloalkyl-$C_{1-3}$-alkyl, $C_{1-6}$-alkyl-CO, $C_{3-6}$-cycloalkyl-CO, $C_{3-6}$-cycloalkyl-$C_{1-3}$-alkyl-CO, $C_{1-6}$-alkyl-$SO_2$, $C_{3-6}$-cycloalkyl-$SO_2$, $C_{3-6}$-cycloalkyl-$C_{1-3}$-alkyl-$SO_2$, phenyl-CO— and phenyl-$SO_2$,
$R^d$ denotes hydrogen or
a group selected from among
F, Cl, Br, I, OH, $C_{1-4}$-alkyl, $C_{1-4}$-alkyl-O, $C_{1-2}$-alkyl-O substituted by 1 to 3 fluorine atoms, $C_{3-7}$-cycloalkyl-O, $C_{3-7}$-cycloalkyl-$C_{1-4}$-alkyl-O, tetrahydrofuran-3-yl-O, tetrahydropyran-3-yl-O, tetrahydro-pyran-4-yl-O, tetrahydrofuranyl-$C_{1-4}$-alkyl-O— and tetrahydropyranyl-$C_{1-4}$-alkyl-O,
or
$R^4$—$C_{1-4}$-alkyl, while the linking of the groups $R^4$ may take place via each C atom of the alkyl group,
or
$R^4$—$C_{2-4}$-alkyl-O, wherein the group $R^4$ is separated from the oxygen atom by at least 2 C atoms,
or
a group selected from among
pyrrolidin-2-yl-$C_{1-4}$-alkyl-O, pyrrolidin-3-yl-$C_{1-4}$-alkyl-O, piperidin-2-yl-$C_{1-4}$-alkyl-O, piperidin-3-yl-$C_{1-4}$-alkyl-O, piperidin-4-yl-$C_{1-4}$-alkyl-O, azepan-2-yl-$C_{1-4}$-alkyl-O, azepan-3-yl-$C_{1-4}$-alkyl-O, azepan-4-yl-$C_{1-4}$-alkyl-O, morpholin-2-yl-$C_{1-4}$-alkyl-O, morpholin-3-yl-$C_{1-4}$-alkyl-O, 1-($C_{1-3}$-alkyl)-pyrrolidin-2-yl-$C_{1-4}$-alkyl-O, 1-($C_{1-3}$-alkyl)-pyrrolidin-3-yl-$C_{1-4}$-alkyl-O, 1-($C_{1-3}$-alkyl)-piperidin-2-yl-$C_{1-4}$-alkyl-O, 1-($C_{1-3}$-alkyl)-piperidin-3-yl-$C_{1-4}$-alkyl-O, 1-($C_{1-3}$-alkyl)-piperidin-4-yl-$C_{1-4}$-alkyl-O, 1-($C_{1-3}$-alkyl)-azepan-2-yl-$C_{1-4}$-alkyl-O, 1-($C_{1-3}$-alkyl)-azepan-3-yl-$C_{1-4}$-alkyl-O, 1-($C_{1-3}$-alkyl)-azepan-4-yl-$C_{1-4}$-alkyl-O, 4-($C_{1-3}$-alkyl)-morpholin-2-yl-$C_{1-4}$-alkyl-O— and 4-($C_{1-3}$-alkyl)-morpholin-3-yl-$C_{1-4}$-alkyl-O, while $R^4$ denotes a group, which may be identical or different, selected from among OH, $C_{1-3}$-alkyl-O, $C_{3-6}$-cycloalkyl-O, $NH_2$, $C_{1-3}$-alkyl-NH, $(C_{1-3}$-alkyl$)_2$N, (2-methoxyethyl)$_2$N, pyrrolidin-1-yl, piperidin-1-yl, azepan-1-yl, morpholin-4-yl, 1,4-oxazepan-4-yl, 2-oxa-5-aza-bicyclo[2,2,1]hept-5-yl, 3-oxa-8-aza-bicyclo[3.2.1]oct-8-yl, 8-oxa-3-aza-bicyclo[3.2.1]oct-3-yl, piperazin-1-yl, 4-($C_{1-3}$-alkyl)-piperazin-1-yl, 1,4-diazepan-1-yl, 4-($C_{1-3}$-alkyl)-1,4-diazepan-1-yl, HCO—NH, $C_{1-4}$-alkyl-CO—NH, $C_{1-3}$-alkyl-O—$C_{1-3}$-alkyl-CO—NH, $C_{1-4}$-alkyl-O—CO—NH, $H_2$NCONH, $C_{1-3}$-alkyl-NH—CO—NH, $(C_{1-3}$-alkyl$)_2$N—CONH, pyrrolidin-1-yl-CO—NH, piperidin-1-yl-CO—NH, piperazin-1-yl-CO—NH, 4-($C_{1-3}$-alkyl)-piperazin-1-yl-CO—NH, morpholin-4-yl-CO—NH— and $C_{1-4}$-alkyl-$SO_2$—NH, while the pyrrolidinyl, piperidinyl, azepan-1-yl, piperazinyl, 1,4-diazepan-1-yl, morpholinyl- and 1,4-oxazepan-4-yl groups mentioned above in the definition of the group $R^d$ may each additionally be substituted by one or two $C_{1-3}$-alkyl groups, and wherein the above-mentioned phenyl groups are mono- or disubstituted by groups $R^5$, wherein $R^5$ denotes hydrogen, or a group, which may be identical or different, selected from among F, Cl, Br, I, OH, CN, $C_{1-3}$-alkyl, $C_{1-3}$-alkyl-O, $CHF_2$, $CF_3$, —O—$CHF_2$ and —O—$CF_3$, and unless stated otherwise, the above-mentioned alkyl groups may be straight-chain or branched, A denotes —CO or —$C_1$-$C_3$-alkylene, while the —$C_1$-$C_3$-alkylene-group may be 1-, 2-, 3- or 4-substituted by a group $R^6$, and $R^6$ which may be identical or different, denotes hydrogen, or a group selected from among OH, $C_1$-$C_4$-alkyl and —O—$C_1$-$C_4$-alkyl or a tautomer, stereoisomer, mixture, or salt thereof.

2. A method for the treatment of viral infection and exacerbation in respiratory diseases comprising administering to a patient in need thereof a therapeutically effective amount of a compound selected from the group consisting of (1.86) anti-9-[4-(3-chloro-2-fluoro-phenylamino)-7-methoxy-quinazolin-6-yloxy]-1,4-diaza-spiro[5.5]undecan-5-one, (1.87) syn-9-[4-(3-chloro-2-fluoro-phenylamino)-7-methoxy-quinazolin-6-yloxy]-1,4-diaza-spiro[5.5]undecan-5-one, (1.88) anti-9-[4-(3-chloro-2-fluoro-phenylamino)-7-methoxy-quinazolin-6-yloxy]-1-methyl-1,4-diaza-spiro[5.5]undecan-5-one, (1.89) anti-9-[4-(3-chloro-2-fluoro-phenylamino)-7-methoxy-quinazolin-6-yloxy]-1,4-dimethyl-1,4-diaza-spiro[5.5]undecan-5-one, (1.90) anti-8-[4-(3-chloro-2-fluoro-phenylamino)-7-methoxy-quinazolin-6-yloxy]-1,3-diaza-spiro[4.5]decan-2,4-dione, (1.91) syn-8-[4-(3-chloro-2-fluoro-phenylamino)-7-methoxy-quinazolin-6-yloxy]-1,3-diaza-spiro[4.5]decan-2,4-dione, and the tautomers, racemates, enantiomers, diastereomers and pharmacologically acceptable acid addition salts thereof.

3. The method according to claim 1, wherein the respiratory disease is selected from the group consisting of asthma, chronic obstructive pulmonary disease (COPD), chronic bronchitis, otitis media, sinusitis, pneumonia, lung fibrosis and cystic fibrosis.

4. The method according to claim 1, wherein said treatment is by airway delivery.

5. The method according to claim 1, wherein said treatment is by oral delivery.

6. The method according to claim 1, wherein said virus is selected from the group consisting of Rhinovirus, influenza virus, parainfluenza virus, coronavirus, adenovirus, respiratory syncytial virus, picornavirus, metapneumovirus, hantavirus, measles virus, Epstein-Barr virus, herpes simplex virus and cytomegalovirus.

\* \* \* \* \*

UNITED STATES PATENT AND TRADEMARK OFFICE
CERTIFICATE OF CORRECTION

| | | |
|---|---|---|
| PATENT NO. | : 8,629,153 B2 | Page 1 of 1 |
| APPLICATION NO. | : 13/061753 | |
| DATED | : January 14, 2014 | |
| INVENTOR(S) | : Jung | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 313 days.

Signed and Sealed this
Seventh Day of April, 2015

Michelle K. Lee
*Director of the United States Patent and Trademark Office*